United States Patent

Kordonski et al.

[11] Patent Number: 5,951,369
[45] Date of Patent: Sep. 14, 1999

[54] SYSTEM FOR MAGNETORHEOLOGICAL FINISHING OF SUBSTRATES

[75] Inventors: William I. Kordonski; Donald Golini, both of Rochester; Stephen Hogan, Rush; Paul R. Dumas, Rochester, all of N.Y.

[73] Assignee: QED Technologies, Inc., Rochester, N.Y.

[21] Appl. No.: 09/226,326

[22] Filed: Jan. 6, 1999

[51] Int. Cl.$^6$ ...................................................... B24B 49/00
[52] U.S. Cl. .................................. 451/5; 451/36; 451/60; 451/87
[58] Field of Search .................................. 456/5, 36, 41, 456/60, 87, 93; 137/92

[56] References Cited

U.S. PATENT DOCUMENTS

| | | |
|---|---|---|
| 5,449,313 | 9/1995 | Kordonsky et al. . |
| 5,525,249 | 6/1996 | Kordonsky et al. . |
| 5,569,061 | 10/1996 | Kremen ..................................... 451/93 |
| 5,577,948 | 11/1996 | Kordonsky et al. . |
| 5,616,066 | 4/1997 | Jacobs et al. . |
| 5,775,976 | 7/1998 | Kremen et al. ............................ 451/36 |
| 5,795,212 | 8/1998 | Jacobs et al. . |
| 5,813,901 | 9/1998 | Kremen ..................................... 451/28 |
| 5,839,944 | 11/1998 | Jacobs et al. ................................ 451/8 |

*Primary Examiner*—David A. Scherbel
*Assistant Examiner*—Dung Van Nguyen
*Attorney, Agent, or Firm*—Harris Beach & Wilcox, LLP

[57] ABSTRACT

An improved system for increasing the effectiveness of magnetorheological finishing of a substrate. An inline flowmeter is close-loop linked to the rotational speed of a pressurizing pump to assure that the flow of magnetorheological fluid (MRF) to the work zone is constant. A simplified capillary viscometer is disposed in the fluid delivery system at the exit thereof onto the wheel surface. Output signals from the flowmeter and the viscometer pressure sensor are sent to a computer which calculates the viscosity of MRF being delivered to the work zone and causes replenishment of carrier fluid to the work-concentrated MRF to return the viscosity to aim to assure that a constant concentration of magnetic solids is being provided to the work zone. Asymmetric pole pieces for the field magnet at the work zone extend the magnetic field along the wheel surface upstream of the work zone to permit full magnetic stiffening of the MRF before it engages the work piece, while minimizing fringing field in the vicinity of the viscometer, and to shorten the magnetic field along the wheel surface downstream of the work zone.

20 Claims, 5 Drawing Sheets

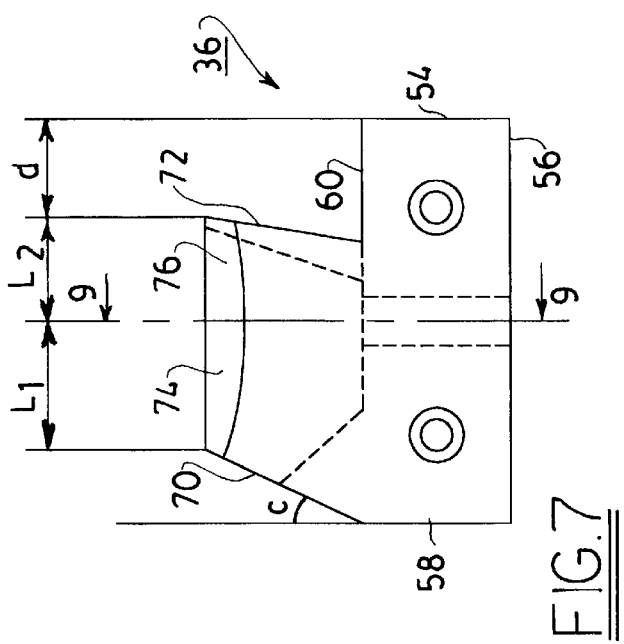
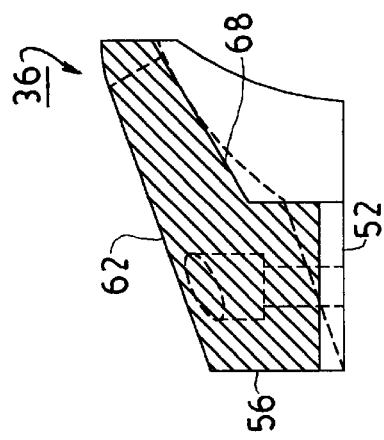
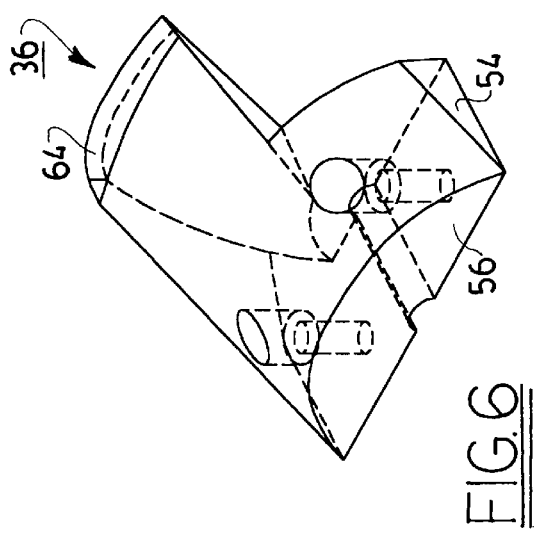
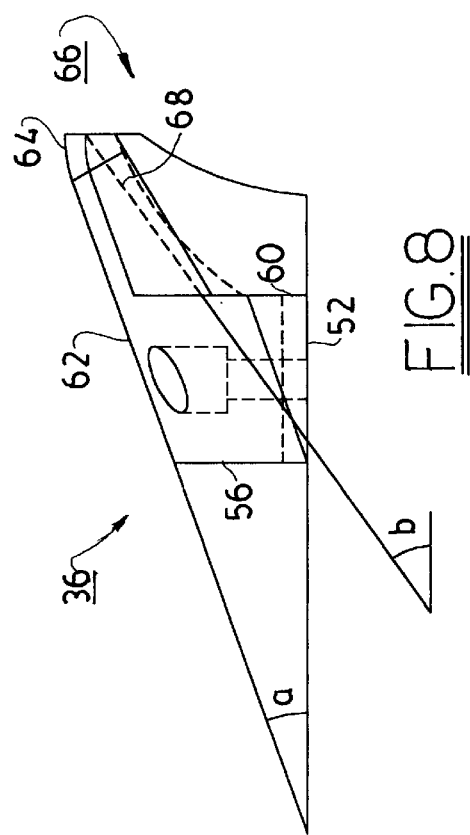
FIG.6
FIG.7
FIG.8
FIG.9

SYSTEM FOR MAGNETORHEOLOGICAL FINISHING OF SUBSTRATES

BACKGROUND OF THE INVENTION

1. Field of the Invention

The present invention relates to systems for slurry-based abrasive finishing and polishing of substrates, more particularly to such systems employing magnetorheological fluids (MRF), and most particularly to an improved system wherein the magnetic field is optimally shaped through novel shaping of the pole pieces and wherein the viscosity and flow rate of recirculated MRF is dynamically controlled through use of a novel capillary viscometer and inline flowmeter.

2. Discussion of the Related Art

Use of magnetically-stiffened magnetorheological fluids for abrasive finishing and polishing of substrates is well known. Such fluids, containing magnetically-soft abrasive particles dispersed in a liquid carrier, exhibit magnetically-induced thixotropic behavior in the presence of a magnetic field. The apparent viscosity of the fluid can be magnetically increased by many orders of magnitude, such that the consistency of the fluid changes from being nearly watery to being a very stiff paste. When such a paste is directed appropriately against a substrate surface to be shaped or polished, for example, an optical element, a very high level of finishing quality, accuracy, and control can be achieved.

U.S. Pat. Nos. 5,449,313 issued Sep. 12, 1995 and 5,577,948 issued Nov. 26, 1996, both to Kordonsky et al. disclose magnetorheological polishing devices and methods.

U.S. Pat. No. 5,525,249 issued Jun. 11, 1996 to Kordonsky et al. discloses magnetorheological fluids and methods of making thereof.

U.S. Pat. No. 5,616,066 issued Apr. 1, 1997 to Jacobs et al. discloses methods and apparatus for magnetorheological finishing of edges of optical elements.

U.S. Pat. No. 5,795,212 issued Aug. 18, 1998 to Jacobs et al., the disclosure of which is hereby incorporated by reference, discloses methods, fluids, and apparatus for deterministic magnetorheological finishing of substrates. This patent is referred to herein as "U.S. Pat. No. '212."

In a typical magnetorheological finishing system, such as is disclosed in the U.S. Pat. No. '212, a work surface comprises a vertically-oriented wheel having an axially-wide rim which is undercut symmetrically about a hub. Specially shaped magnetic pole pieces, which are symmetrical about a vertical plane containing the axis of rotation of the wheel, are extended toward opposite sides of the wheel under the undercut rim to provide a magnetic work zone on the surface of the wheel, preferably at about the top-dead-center position. The surface of the wheel may be flat, i.e., a cylindrical section, or it may be convex, i.e., a spherical equatorial section, or it may be concave. The convex shape can be particularly useful as it permits finishing of concave surfaces having a radius longer than the radius of the wheel.

Mounted above the work zone is a substrate receiver, such as a chuck, for extending a substrate to be finished into the work zone. The chuck is programmably manipulable in a plurality of modes of motion and is preferably controlled by a programmable controller or a computer.

Magnetorheological fluid having a predetermined concentration of particles which are magnetically soft is extruded in a non-magnetized state, typically from a shaping nozzle, as a ribbon onto the work surface of the wheel, which carries it into the work zone where it becomes magnetized to a pasty consistency. In the work zone, the pasty MRF does abrasive work on the substrate and becomes heated thereby. The heating and exposure of the MRF causes some evaporation of carrier fluid and a consequent concentrating of the MRF. Exiting the work zone, the concentrated fluid becomes non-magnetized again and is scraped from the wheel work surface for recirculation and reuse.

Fluid delivery to, and recovery from, the wheel is managed by a closed fluid delivery system. MRF is withdrawn from the scraper by a suction pump and sent to a tank where its temperature is measured and adjusted to aim. Recirculation from the tank to the nozzle, and hence through the work zone, at a specified flow rate is accomplished by setting the speed of rotation of a pressurizing pump, typically a peristaltic pump. The concentration of solids in the MRF as discharged onto the wheel is an important factor in controlling the rate of abrasive milling of a substrate in the work zone. Viscosity being a direct correlate of concentration, it is highly desirable to dynamically adjust the viscosity of the concentrated MRF being recirculated to an aim value during use. In the line between the pump and nozzle is a viscometer comprising a length of capillary tubing having upstream and downstream pressure sensors. At a constant fluid flow rate, the pressure drop through the capillary tubing, that is, the pressure difference between the two pressure sensors, is proportional to the viscosity of the fluid. An increase in pressure drop is inferred to mean an increase in viscosity and is used to cause replenishment of carrier fluid into the MRF in the tempering tank to reduce the apparent viscosity to aim.

OBJECTS OF THE INVENTION

Several problems have been encountered in using the U.S. Pat. No. '212 disclosure to finish substrates. It has been found that finishing effectiveness as measured by rate of removal of substrate material can be reduced by failure to fully stiffen the MRF ribbon before it engages the workpiece in the work zone and further by failure to continuously deliver an MRF ribbon of substantially uniform thickness and solids concentration to the magnetic field in the work zone. An MRF finishing system in accordance with the present invention comprises novel solutions to these problems.

Regarding the problem of providing a ribbon of constant thickness and solids concentration, in the known art of fluid delivery, pump output can change over time, especially from a peristaltic pump which is subject to progressive fatigue of resilient tubing being peristaltically compressed. Erroneous flow will lead to a false inference, either high or low, of viscosity in the U.S. Pat. No. '212 viscometer and consequent incorrect replenishment of carrier fluid. Thus, it is an object of the invention to provide an improved MRF finishing system wherein the actual volumetric fluid flow rate is measured and controlled independently of the indicated speed of a pressurizing pump and is used in determining the replenishment rate of carrier fluid.

Regarding the accurate online measurement of MRF viscosity, the capillary tubing of the U.S. Pat. No. '212 viscometer must be physically remote from the region near the work zone to avoid fringing field interaction with the MRF in the tubing which can lead to incorrect inference of viscosity and consequent incorrect replenishment of carrier fluid. This placement within the delivery system requires use of two pressure sensors to establish a pressure drop. Further, it is desirable to know the viscosity at the point at which the MRF exits the delivery system onto the wheel. Thus, it is a further object of the invention to provide an improved and simplified MRF finishing system wherein only a single pressure sensor is required and wherein the viscosity is measured at the exit of the delivery system. Regarding the need to fully stiffen the MRF before engaging it with the workpiece, the symmetrical pole pieces of the U.S. Pat. No. '212 magnet create a work zone which is symmetrical about top-dead-center and about the position of a substrate workpiece in the work zone. Such symmetry does not take into consideration magnetic hysteresis in the stiffening and relaxation of the MRF, thereby reducing the potential effectiveness of an MRF finishing system. Thus, it is a still further object of the invention to provide an improved MRF finishing system having asymmetrical pole pieces whereby the MRF is fully stiffened on the wheel prior to engagement with a workpiece and is relaxed shortly after disengagement with a workpiece.

BRIEF DESCRIPTION OF THE INVENTION

Briefly described, an improved system for magnetorheological finishing of a substrate in accordance with the invention comprises a fluid recirculation and management system and magnetic pole pieces similar to those disclosed in U.S. Pat. No. '212 but comprising the following important and novel improvements.

First, an inline flowmeter is provided in the fluid recirculation system, preferably a magnetic-induction flowmeter, preferably but not necessarily close-loop linked to a flow controlling parameter, for example, rotational speed of a pressurizing pump, to measure the actual flow rate and preferably to assure that fluid flow rate is constant, independent of viscosity of the fluid being pumped. Such a flowmeter is preferably insensitive to changes in fluid viscosity over the range of flows of interest.

Second, a simplified and novel capillary viscometer comprising a single pressure sensor at the entrance to a capillary section and having magnetic shielding of the capillary tubing is disposed in the fluid delivery system at the exit thereof onto the wheel surface, obviating thereby the need for a second pressure sensor. Output signals from the flowmeter and the viscometer pressure sensor are inputted to an algorithm in a computer which calculates the apparent viscosity of MRF being delivered to the wheel and controls the rate of replenishment of carrier fluid to recirculating MRF in a mixing chamber ahead of the viscometer to adjust the apparent viscosity to aim.

Third, novel asymmetric pole pieces are provided which extend the magnetic field along the wheel surface upstream of the work zone to permit full magnetic stiffening of the MRF before engaging the work piece, while minimizing fringing field in the vicinity of the viscometer, and which shorten the magnetic field along the wheel surface downstream of the work zone.

BRIEF DESCRIPTION OF THE DRAWINGS

The foregoing and other objects, features, and advantages of the invention, as well as presently preferred embodiments thereof, will become more apparent from a reading of the following description in connection with the accompanying drawings in which:

FIG. 6 is an isometric view of a right side asymmetrical pole piece in accordance with the invention;

FIG. 7 is a plan view of the pole piece shown in FIG. 6;

FIG. 8 is a side view of the pole piece shown in FIG. 6;

FIG. 9 is a vertical cross-sectional view taken along line 9—9 in FIG. 7;

DETAILED DESCRIPTION OF THE INVENTION

Figure 1:
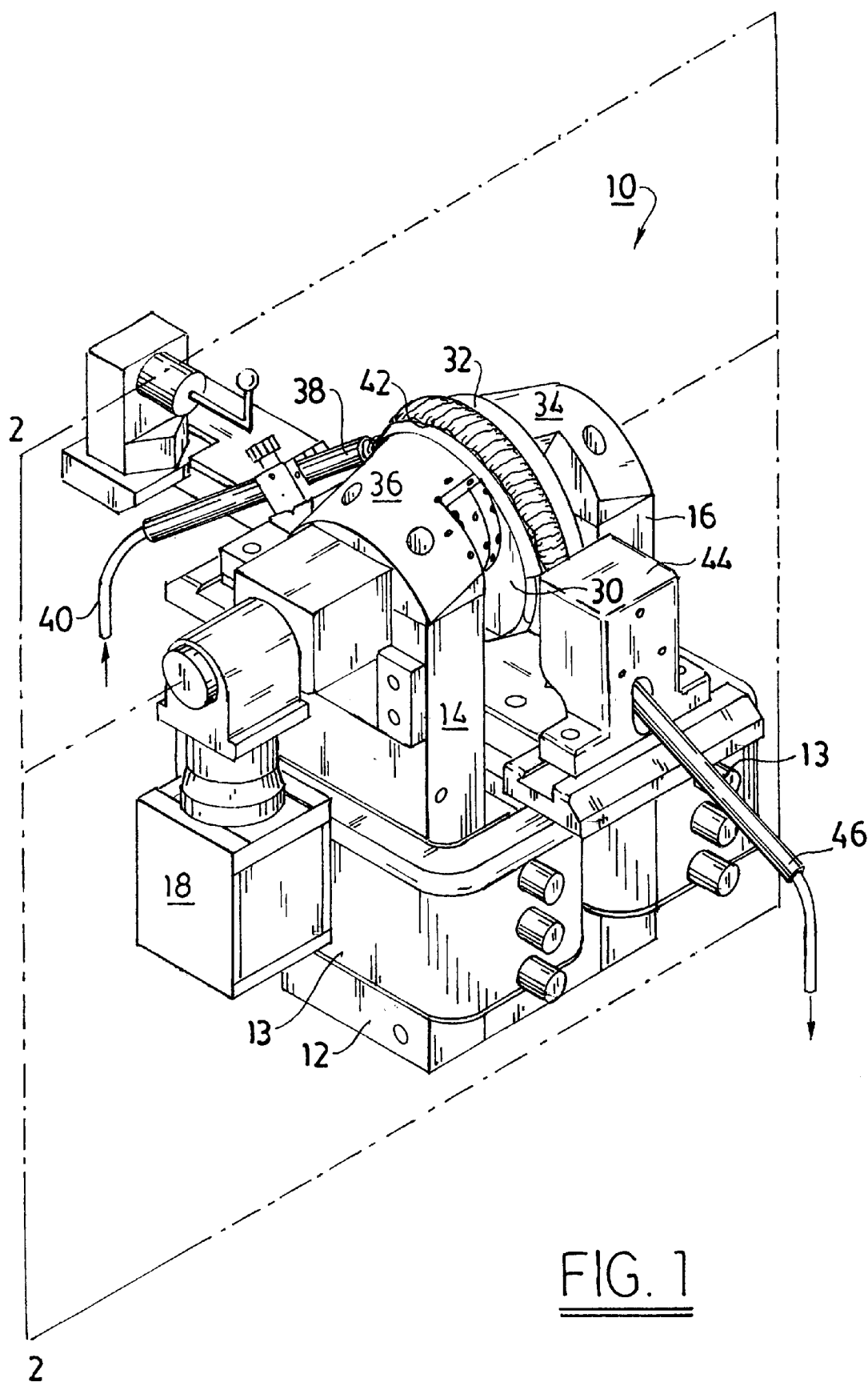
FIG. 1 is an isometric view of the mechanical assembly portion of a substrate finishing apparatus in accordance with the invention.
Figure 2:
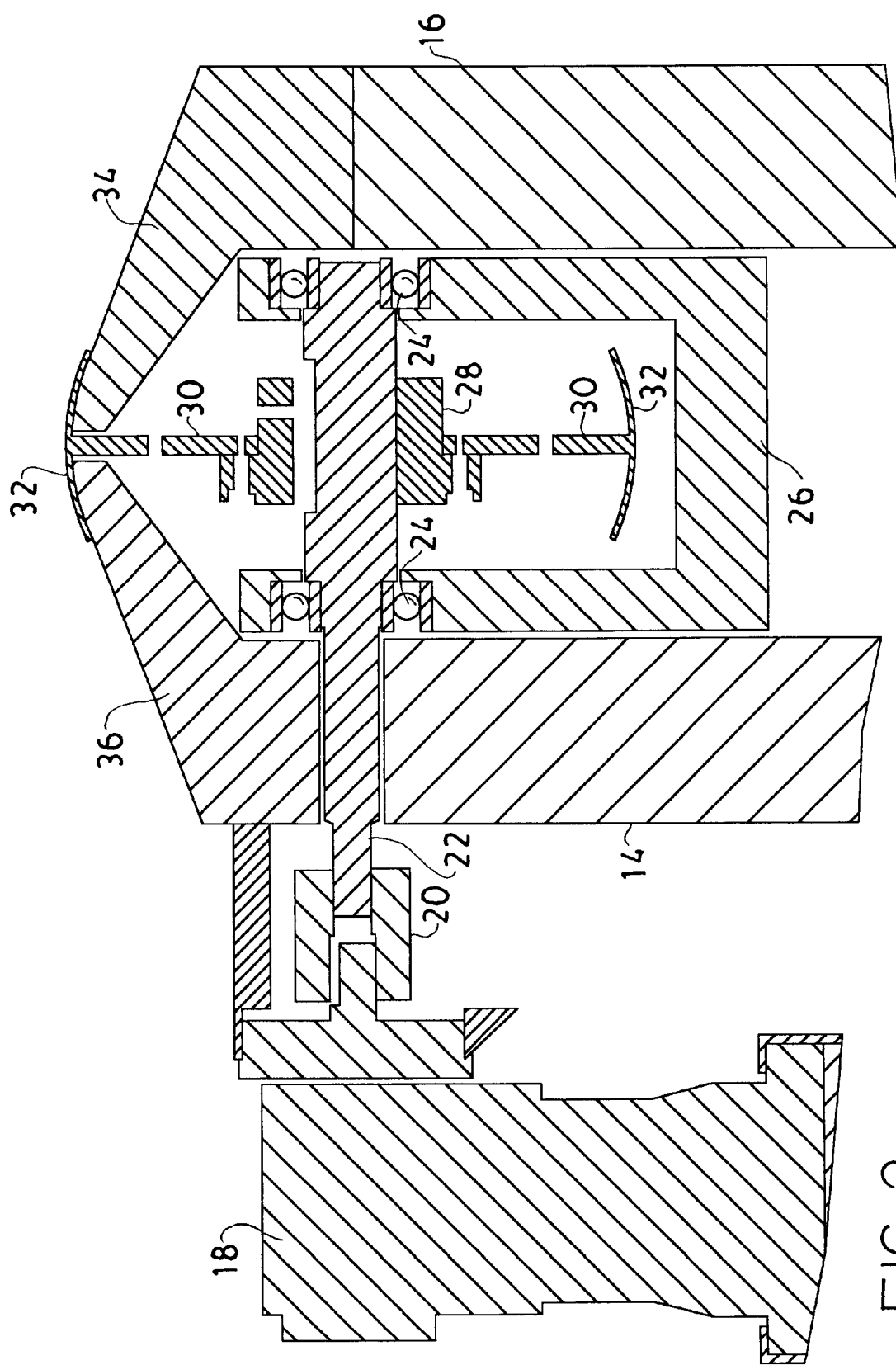
FIG. 2 is a vertical cross-sectional view taken through plane 2—2 in FIG. 1.

In FIGS. 1 and 2 is shown the overall layout of a mechanical assembly portion 10 of a system in accordance with the invention for magnetorheological finishing of a substrate. Portion 10 includes a base 12 which supports the core of a magnet, preferably the core and windings 13 of an electromagnet, and supports left and right magnet yoke members 14,16, respectively, which are connected conventionally to the core. The layout of portion 10 is similar to the layout disclosed in U.S. Pat. No. '212, with improvements as described below. Yoke 14 supports a motor drive unit 18 coupled via coupling 20 to a shaft 22 journalled in bearings 24 and supported by a pedestal 26. Drive unit 18 is controlled by a drive controller (not shown) in conventional fashion to control the rotational speed of the drive at a desired aim. Shaft 22 is rotatably coupled to the hub 28 of a carrier wheel flange 30 supporting a peripheral surface 32 which extends axially of flange 30 to both sides thereof, preferably symmetrically. Surface 32, which is the work surface of the apparatus, also known as the carrier surface, may be substantially flat, i.e., have curvature in only the circumferential direction, defining a cylindrical section, or surface 32 may also be arcuate in the axial direction, defining a concavity or a convexity (as shown in FIG. 2). Mounted on yoke members 14,16 are left and right magnet polepieces 34,36, respectively. The magnet may be alternatively oriented and operated such that polepieces 34,36 are magnetically north and south or south and north, respectively, to equal effect. An application nozzle 38 is connected to supply line 40 for providing a ribbon 42 of MRF onto moving work surface 32, and a scraper 44 is connected to return line 46 for removing MRF from work surface 32 and returning MRF to a recirculating and conditioning system (not shown in FIGS. 1 and 2). Scraper 44 is preferably magnetically shielded.

Figure 5:
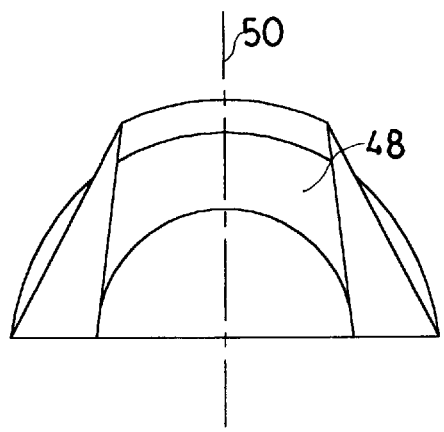
FIG. 5 is an elevational view of a prior art right side symmetrical pole piece.

Referring to FIG. 5, prior art polepiece 48 is symmetrical about symmetry plane 50 corresponding to plane 2—2 in FIG. 1; therefore, in a prior art assembly, the left and right polepieces are identical and interchangeable. Since the preferable work zone for abrasive finishing and polishing is centered at the top-dead-center position on the carrier wheel, the work zone is thus centered in the magnetic field produced by prior art polepieces 48. However, the magnetorheological response of MRF entering or leaving the magnetic field is not instantaneous, such that in the prior art apparatus the MRF may not be fully stiffened when it is impinged onto the workpiece to be finished, reducing the abrasive impact of the MRF particles, and further, the MRF may still possess magnetically-induced stiffness when it reaches the scraper, interfering with removal of the MRF from the carrier surface.

Figure 3:
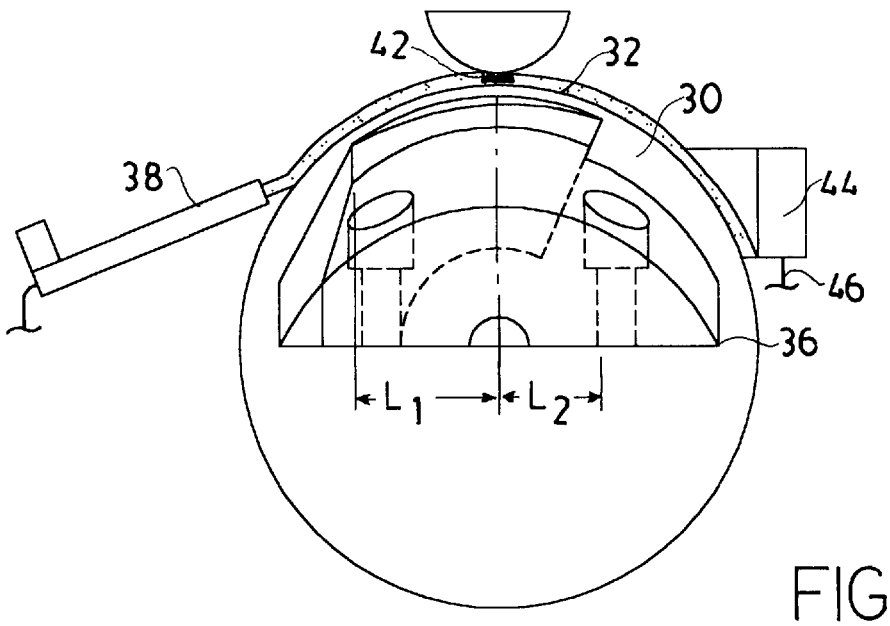
FIG. 3 is a right side schematic elevational view of a portion of the apparatus shown in FIG. 1, showing the relationship of an asymmetric pole piece to the rim of the carrier wheel and to the preferred location of a workpiece in the work zone.
Figure 4:
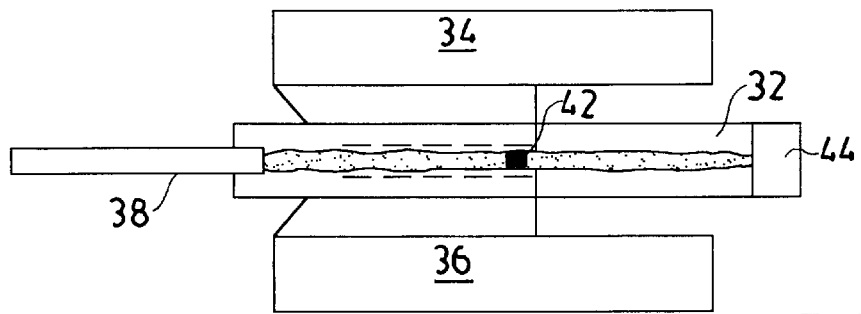
FIG. 4 is a plan view of the apparatus shown in FIG. 3 with the workpiece removed for clarity of illustration.

Magnetic field application to the MRF magnetizes the magnetic particles and triggers the formation of a field-oriented structure which defines the stiffened fluid. Whereas magnetic particle magnetization occurs very rapidly (in about $10^{-9}$ seconds), the formation of structure is significantly slower (typically $10^{-3}$ to $10^{-4}$ seconds). The characteristic time $T_{char}$ of structure formation depends on properties of the MRF. To achieve maximal fluid stiffening at the work zone, the time of fluid transportation $T_{trans}$ from entry into the magnetic field to reaching the work zone should be greater than the characteristic time of the MRF ($T_{trans} > T_{char}$). The fluid transportation time is the distance $L_1$ from the pole piece entry edge to the center of the work zone (as shown in FIGS. 3 and 7) divided by the linear speed U of the wheel surface ($L_1/U > T_{char}$). In contrast, as the MRF leaves the work zone it should be demagnetized as soon as possible to facilitate removal of the spent MRF from the wheel; therefore, the distance $L_2$ from the center of the work zone to the polepiece outlet edge should be minimized, resulting in an asymmetric pole piece. Selection of lengths $L_1$ and $L_2$ is governed by the magnetomechanical (viscosity) properties of the MRF being used and the speed of the wheel.

A pair of truly optimal polepieces provide the following benefits: a) maximal fluid stiffening at the work zone; b) maximal magnetic field strength at the work zone; c) smooth magnetic field gradient at the zone of fluid deposition onto the wheel; and d) sharp magnetic field gradient and minimal magnetic field strength at the zone of fluid pick-up.

Improved polepieces 34,36 in accordance with the invention are asymmetric about plane 2—2 in FIG. 1, as well as every other plane which includes the axis of shaft 22, to extend the magnetic field along the carrier surface ahead of the work zone and to shorten the magnetic field after the work zone. This assures that the MRF is fully stiffened when it enters the work zone and that it is fully relaxed when it reaches the scraper. It should be understood that polepieces 34,36 are substantially mirror images of each other. Thus, the following description, directed specifically to right polepiece 36, is equally applicable to left polepiece 34.

Referring to FIGS. 3–4 and 6–9, a preferred embodiment of polepiece 36 has a substantially rectangular base 52 conformable with the upper surface of yoke member 16. Vertical sides 54,56,58,60 are substantially planar extensions of the vertical sides of polepiece 36. Outer surface 62 is a cylindrical section inclined to base 52 at an angle a. The upper surface 64 of nose portion 66 is concentric with surface 32, and thus may be a spherical section, as shown in FIG. 1, or may be cylindrical or concave, as required by the shape selected for surface 32. The undersurface 68 is a conical section having the apex pointed away from wheel 30 and having a side thereof inclined to base 52 at an angle b which is greater than angle a. The entering flank 70 is turned at an angle c, preferably about 25°, to help confine and focus the magnetic field within the polepiece. The exiting flank 72 is relieved by a distance d such that surface 64 is asymmetrically disposed about plane 2—2, shown in FIG. 1 which corresponds to plane 50 in FIG. 7, the entering portion 74 of surface 64 being longer ($L_1$) in the direction of travel of surface 32 than exiting portion 76 ($L_2$). The cross-sectional view of polepiece 36 as shown in FIG. 9 is substantially the same as is shown in FIG. 1.

Figure 10:
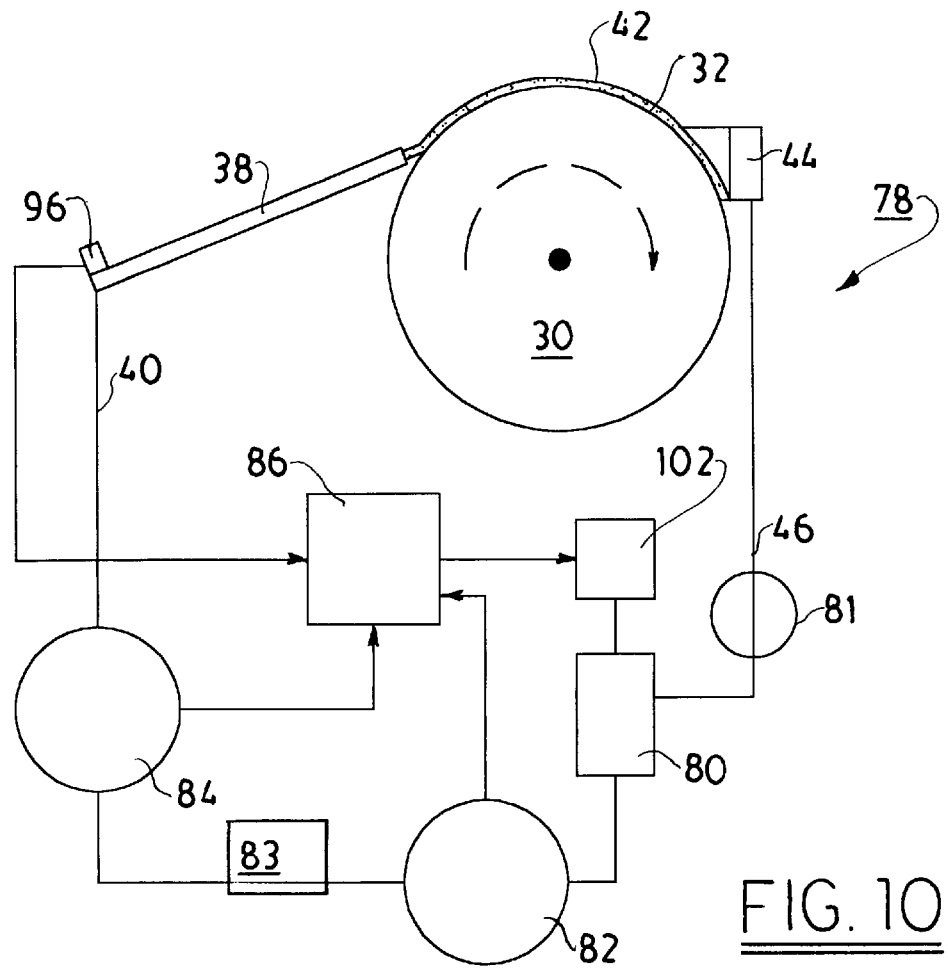
FIG. 10 is a schematic view of a fluid recirculating system in accordance with the invention.
Figure 11:
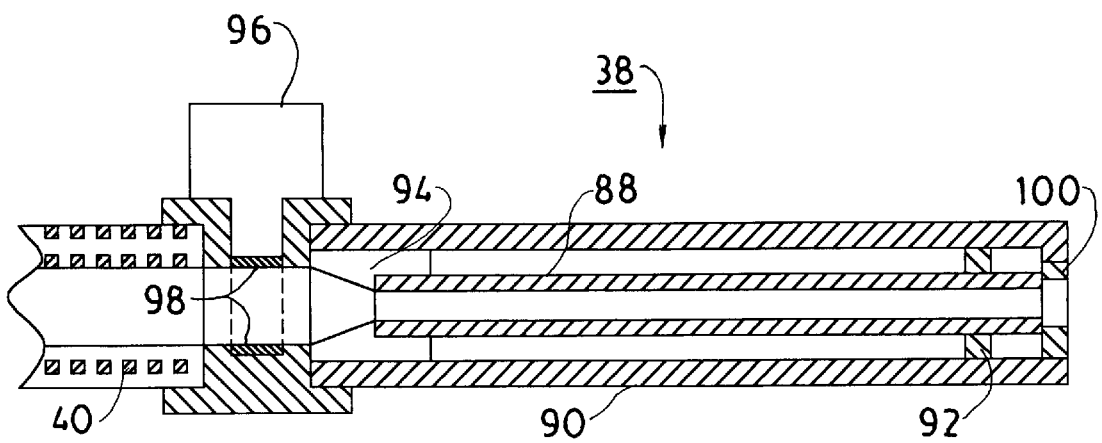
FIG. 11 is a cross-sectional view of a capillary viscometer in accordance with the invention.

Referring now to FIGS. 10 and 11, a closed fluid delivery system 78 is shown for providing MRF to the carrier surface 32 at a constant aim flow rate and viscosity, recovering MRF from the carrier surface, and conditioning recovered MRF for re-use. MRF is scraped from the carrier surface by scraper 44 and returned via line 46 to an inline mixing and tempering chamber 80 wherein agglomerates are broken up, carrier fluid is replenished as described below, and the reconstituted MRF is retempered to an aim temperature. Tempering may be accomplished in known fashion, for example, by means of a tempered water jacket (not shown) surrounding the mixing chamber. In systems wherein chamber 80 is not a closed chamber, it may be necessary to include an additional pump 81 to acquire the spent MRF from scraper 44 and deliver it to chamber 80. Retempered MRF is withdrawn from the mixing chamber by an inline delivery pump 82, for example, a peristaltic pump, and delivered through an inline flowmeter 84, preferably a magnetic-induction flowmeter such as a Rosemount Magnetic Flowmeter Series 8700, available from Fisher Rosemount Corp., Chahassen, Minn., USA. If the output of pump 82 is cyclic, as is well known for peristaltic and other pumps, a pulse dampener 83 as is known in the art may be included in the delivery system downstream of pump 82. Flowmeter 84 and the drive for pump 82 are computationally connected to a computer 86 which sets a flow aim and adjusts the rotational speed of the pump in closed-loop feedback to satisfy the flow aim as measured by the flowmeter. From the flowmeter, MRF passes through nozzle 38 and is discharged for work onto carrier surface 32.

An important improvement in accordance with the invention is the provision of nozzle 38 as a novel inline capillary rheometer or viscometer at the discharge end of the fluid delivery system. Referring to FIG. 11, nozzle 38 comprises a capillary tube 88 formed of a non-magnetic material, for example, copper or ceramic, having a length to diameter ratio preferably greater than about 100:1. Tube 88 is surrounded by a magnetic shield 90 formed preferably of a magnetically soft material, for example, cold rolled steel. Tube 88 and shield 90 are spaced apart by one or more centering washers 92, formed of any suitable non-magnetic material, for example, rubber or plastic, and by a non-magnetic transition piece 94 for smoothly narrowing the MRF flow from the diameter of the supply line 40 to the diameter of tube 88. Preferably, the diameter of tube 88 is selected such that the Reynolds number of the fluid flow conditions through the tube is less than about 100. Disposed between supply line 40 and transition piece 94 is a pressure sensor 96 for sensing line pressure at the entrance to the capillary tube and sending a signal thereof to computer 86. MRF is known to agglomerate readily in stagnant regions, so the pressure sensor must be carefully selected to present a smooth, non-fouling surface to the flow. Preferably, a sensor having a cylindrical diaphragm is used, for example, a Viatran "23" Series Pressure Isolator, available from Viatran Corp., Grand Island, N.Y., USA. Since nozzle 38 is disposed at the end of the delivery line, the pressure drop may be measured relative to ambient pressure, thus only one pressure sensor is required.

System 78 is also provided with a metering pump 98 connected to a source (not shown) of carrier fluid for replenishment of depleted MRF and connected to mixing chamber 80. A suitable metering pump, for example, is Farmington Engineering Solenoid Pump, Part No. D105.55, available from Farmington Engineering, Inc., Madison, Conn., USA.

In operation, MRF is pumped at a desired volumetric flow rate by delivery pump 82 through flowmeter 84 and nozzle 38 onto surface 32. Back pressure in the delivery line 40 is sensed by sensor 96 and transmitted to computer 86. Flow volume is sensed by flowmeter 84 and transmitted to computer 86. Computer 86 is programmed with an algorithm for calculating MRF viscosity as a function of pressure and flowrate through nozzle 38. When a predetermined upper viscosity control limit is exceeded, computer 86 signals metering pump 98 to inject a computer-calculated replenishing amount of carrier fluid into mixing chamber 80 where the fluid is mixed into the recirculating MRF. When aim viscosity is restored, replenishment rate is reduce to an equilibrium at which a constant, low flow of carrier fluid is provided to the mixing chamber which just compensates for the fluid lost to evaporation during a work cycle of the MRF. When a predetermined lower viscosity control limit is exceeded, replenishment is further reduced or stopped altogether to permit work-induced evaporation of carrier fluid from the MRF to gradually increase the viscosity, again until an aim viscosity is restored.

From the foregoing description it will be apparent that there has been provided an improved system for magnetorheological finishing of substrates wherein the effectiveness of finishing is increased over that possible with systems of the prior art through incorporation of: a) novel asymmetrical pole pieces which serve to advance the magnetic stiffening of MRF on the carrier surface ahead of the work zone to assure that the MRF is fully stiffened when it reaches the workpiece and also to advance the magnetic relaxation of MRF after the work zone to facilitate removal of MRF from the carrier surface; and b) a novel inline system for MRF viscosity and flow control which serves to provide to the work zone a substantially constant flowrate of MRF having a substantially constant viscosity, indicative of a constant ribbon height and constant solids concentration and, hence, a constant material removal function from the workpiece. Variations and modifications of the herein described system, in accordance with the invention, will undoubtedly suggest themselves to those skilled in this art. Accordingly, the foregoing description should be taken as illustrative and not in a limiting sense.

What is claimed is:

1. A system for magnetorheological finishing of substrates wherein a fluid delivery system provides a substantially constant flowrate of magnetorheological fluid having a substantially constant viscosity to a work zone at the rim of a carrier wheel, said fluid delivery system having a fluid exit onto said carrier wheel and a fluid entrance from said carrier wheel, comprising:
 a) a pair of substantially mirror-image magnetic polepieces disposed in opposition to each other on opposite sides of said wheel and adjacent said work zone for creating a magnetic field in said work zone for magnetically stiffening said fluid, each of said polepieces being asymmetric in shape with respect to every plane which includes the axis of rotation of said carrier wheel;
 b) a flowmeter disposed in said fluid delivery system for sending a signal indicative of the flowrate of said fluid through said system;
 c) a capillary viscometer disposed at said exit of said fluid delivery system for sending a signal indicative of fluid pressure at the entrance to said viscometer;
 d) means responsive to said flowmeter signal and said pressure signal for controlling the viscosity of fluid passing through said fluid delivery system.

2. A system in accordance with claim 1 wherein said means for controlling viscosity comprises:

a) means for supplying replenishment carrier fluid into said magnetorheological fluid flowing through said fluid delivery system; and
 b) computer means for receiving and using said flow rate signal and said pressure signal to calculate the viscosity of said fluid passing through said capillary viscometer, to calculate a replenishment rate of said carrier fluid required to dilute said magnetorheological fluid flowing through said fluid delivery system to an aim value, and to direct said replenishment supplying means to dispense said carrier fluid into said magnetorheological fluid at said replenishment rate.

3. A system in accordance with claim 1 wherein said flowmeter is a magnetic induction flowmeter.

4. A system in accordance with claim 1 wherein said magnetic field created by said asymmetric polepieces is asymmetric about said work zone, said field being extended along said carrier wheel in a direction opposite to the direction of rotation of said wheel and being shortened along said carrier wheel in said direction of rotation.

5. A system in accordance with claim 1 wherein said capillary viscometer comprises:
 a) a pressure transducer;
 b) a capillary tube; and
 c) a magnetic shield.

6. A system in accordance with claim 5 wherein said pressure transducer is the sole pressure transducer in said viscometer.

7. A system in accordance with claim 5 wherein said pressure transducer comprises a cylindrical sensor.

8. A system in accordance with claim 5 wherein the length of said capillary tube is at least about 100 times the diameter of said tube.

9. A system in accordance with claim 8 wherein said diameter of said capillary tube is selected such that flow of said magnetorheological fluid through said capillary tube has a Reynolds number less than about 100.

10. A system in accordance with claim 5 wherein said capillary tube is formed from a nonmagnetic material.

11. A system in accordance with claim 5 wherein said magnetic shield is formed from a magnetically soft material.

12. A system in accordance with claim 11 wherein said magnetically soft material is cold rolled steel.

13. A system in accordance with claim 5 wherein said capillary viscometer further comprises at least one nonmagnetic spacer between said capillary tube and said magnetic shield.

14. A system in accordance with claim 5 wherein said capillary viscometer further comprises a flow transition portion.

15. A fluid delivery system for providing a substantially uniform flow of magnetorheological fluid having a substantially constant viscosity to a work zone for magnetorheological finishing of substrates, comprising:
 a) a flowmeter for sending a signal indicative of the flow rate of said fluid through said system;
 b) a capillary viscometer disposed at said exit of an fluid delivery system for sending a signal indicative of fluid pressure at the entrance to said viscometer; and
 c) means responsive to said flowmeter signal and said pressure signal for controlling the viscosity of said magnetorheological fluid passing through said fluid delivery system.

16. A system in accordance with claim 15 wherein said means for controlling viscosity comprises:
 a) means for replenishing carrier fluid into said magnetorheological fluid delivery system; and b) computer means for receiving and using said flow rate signal and said pressure signal to calculate the viscosity of said magnetorheological fluid passing through said capillary viscometer, to calculate a replenishment rate of said carrier fluid required to dilute said magnetorheological fluid passing through said magnetorheological fluid delivery system and to direct said replenishing means to dispense said carrier fluid into said magnetorheological fluid at said required replenishment rate.

17. A system in accordance with claim 16 wherein said replenishing means comprises a source of carrier fluid, a metering pump connected to said source, and a chamber connected to said metering pump for receiving said magnetorheological fluid and said carrier fluid.

18. A system in accordance with claim 17 further comprising a first pump for providing said magnetorheological fluid to said chamber.

19. A system in accordance with claim 15 further comprising a second pump for delivering said magnetorheological fluid through said flowmeter and said viscometer.

20. A system in accordance with claim 15 further comprising a pulse dampener.

* * * * *